United States Patent
Thomason

(10) Patent No.: US 6,267,933 B1
(45) Date of Patent: Jul. 31, 2001

(54) METHODS OF PREPARING AND USING ELECTROSTATICALLY TREATED FLUIDS

(76) Inventor: Howard Thomason, 737 Shady View Dr., Canyon Lake, TX (US) 78133

(*) Notice: Subject to any disclaimer, the term of this patent is extended or adjusted under 35 U.S.C. 154(b) by 0 days.

(21) Appl. No.: 09/209,339

(22) Filed: Dec. 11, 1998

Related U.S. Application Data

(63) Continuation-in-part of application No. 08/878,641, filed on Jun. 19, 1997, now abandoned.

(51) Int. Cl.7 .................................................. B01J 19/08
(52) U.S. Cl. ...................................... 422/186.04; 204/663
(58) Field of Search ....................... 422/186.04; 204/663

(56) References Cited

U.S. PATENT DOCUMENTS

| | | |
|---|---|---|
| 3,753,866 | 8/1973 | Myers . |
| 4,012,310 | 3/1977 | Clark . |
| 4,024,047 | 5/1977 | Clark . |
| 4,072,477 | 2/1978 | Hanson . |
| 4,073,712 | 2/1978 | Means . |
| 4,074,983 | 2/1978 | Bakke . |
| 4,419,206 | 12/1983 | Frame . |
| 4,451,341 | 5/1984 | Miller . |
| 4,579,640 | 4/1986 | Eades . |
| 4,719,018 | 1/1988 | Przybylski . |
| 4,822,472 | 4/1989 | Reis . |
| 4,871,450 | 10/1989 | Goodrich . |
| 4,872,959 | 10/1989 | Herbst . |
| 4,886,593 | 12/1989 | Gibbs . |
| 4,902,390 | 2/1990 | Arnesen . |
| 5,106,495 | 4/1992 | Hughes . |
| 5,264,102 | 11/1993 | Eibl . |
| 5,326,446 | 7/1994 | Binger . |
| 5,435,894 | 7/1995 | Hayakawa . |
| 5,447,626 | 9/1995 | Ido . |
| 5,567,293 | 10/1996 | Paleologou . |
| 5,591,317 | 1/1997 | Pitts, Jr. . |
| 5,792,241 | 8/1998 | Browitt . |

*Primary Examiner*—Kishor Mayekar
(74) *Attorney, Agent, or Firm*—George R. Schultz

(57) ABSTRACT

The present invention includes an improved electrostatic device for energizing fluids, in particular water based fluids, which will be used to provide a benefit to living organisms, machinery, processes and substances. The improved device of the invention will include an electrostatic voltage spike signal generator, two or more radio frequency signal generators, one or more antennas, optional one or more signal boosters and a fluid conduit. When fluid is treated with the improved device of the invention, the fluid will become energized and can be used to provide significant benefits in applications such as milk production, flower production, fruit production, crop production, vegetable production, shrimp production, egg production, meat production, gasoline combustion, waste fluid combustion, scale removal, water purification, fluid tracking, fluid sterilization and more.

9 Claims, 7 Drawing Sheets

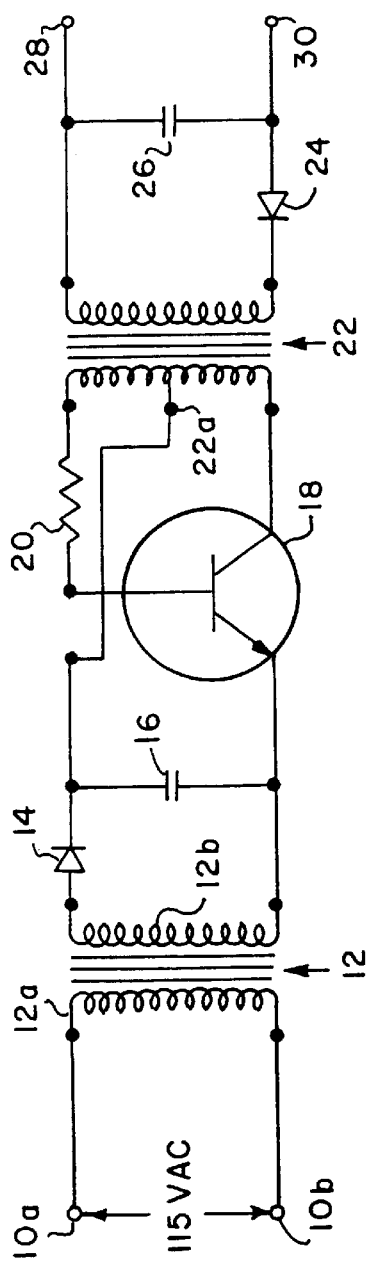
FIG. 1
(PRIOR ART)
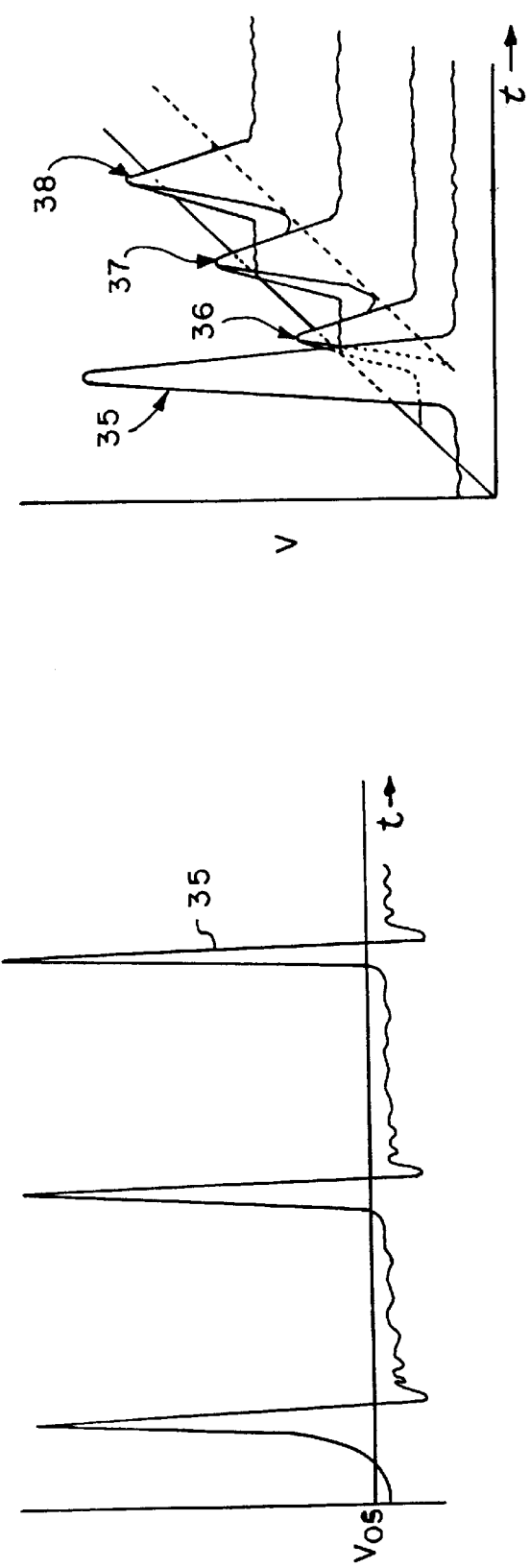
FIG. 2a
(PRIOR ART)
FIG. 2b
(PRIOR ART)

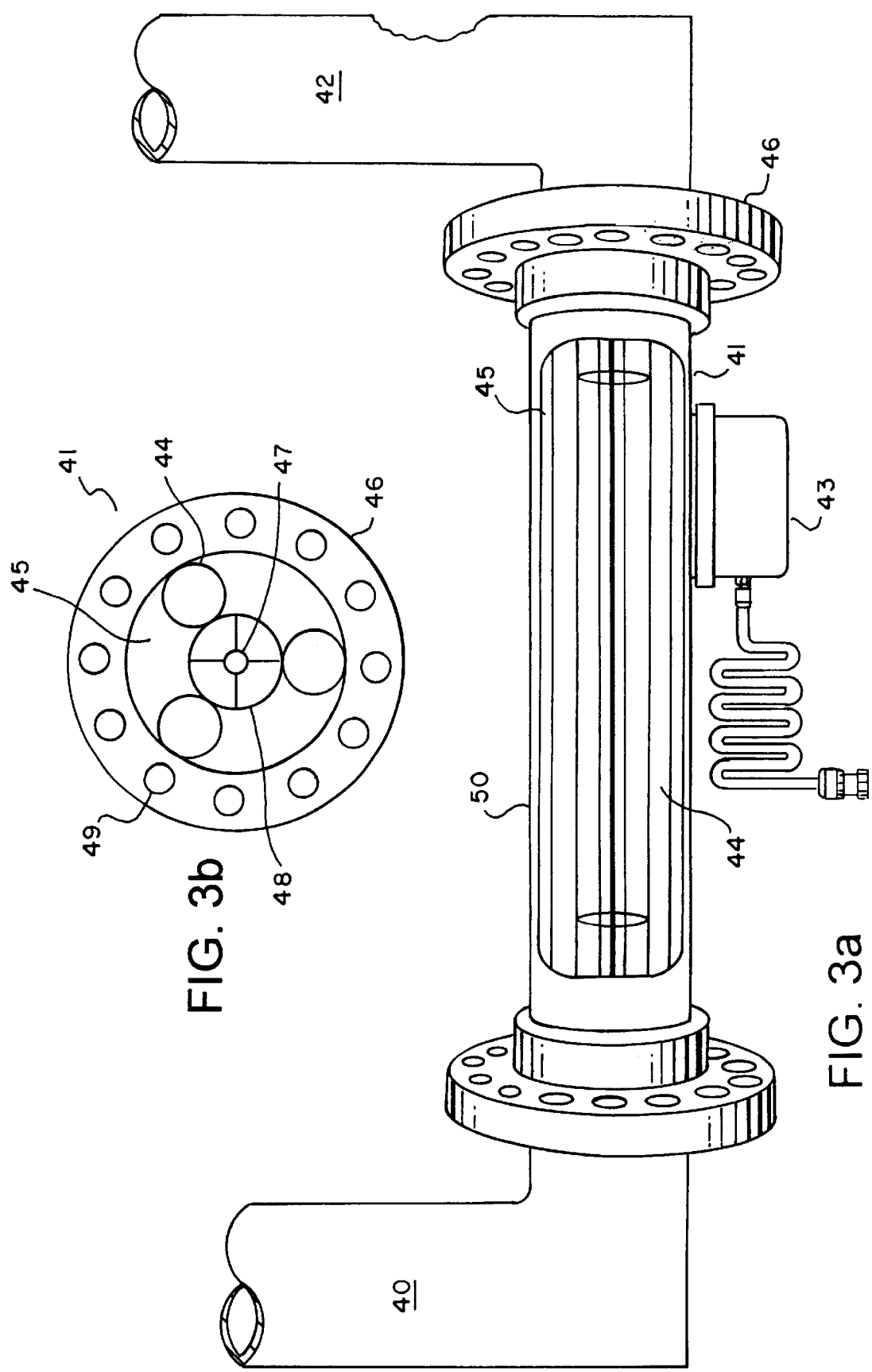

METHODS OF PREPARING AND USING ELECTROSTATICALLY TREATED FLUIDS

This application is a continuation-in-part of application Ser. No. 08/876,641, filed on Jun. 19, 1997, now abandoned.

TECHNICAL FIELD OF THE INVENTION

The present invention relates to methods of preparing and using electrostatically treated fluids, such as water, and to devices for preparing such fluids. Once the fluid has been treated with the apparatus of the invention, it is useful in various applications, provides measurable benefits to animals, plants, aquaculture and equipment and improves a number of industrial/commercial processes.

BACKGROUND OF THE INVENTION

Fluids, such as water, are essential to animals and plants and are essential in many processes. However, many fluids, even common tap water, contain impurities or other properties that reduce the beneficial effects the fluid can provide. Many of these impurities can also detract from the health of living organisms using the fluid and can also inhibit the ability of the organisms to transport waste out of their systems. For industrial processes, these impurities can also cause the buildup of scale in pipes.

The use of electricity, magnetic energy and/or electrons (negatively charged particles) to prevent or remove scale build up in pipes and fluid, in particular water, handling equipment is known. The first, and least effective, is the magnetic unit which fits around the water line. This device takes advantage of a simple magnet with one pole of the magnet, e.g. north, on one side of the water pipe and the opposite pole on the opposite side of the water line. The presence of the magnet essentially creates a minor directing force across the water line. The presence of the magnetic flux will cause charged particles in the water. The particles align themselves in accordance to their charge and that of the magnet. The effect is neither stable nor long lasting as it is quickly lost as the treated water passes through a hot water-tank or is subject to turbulent flow patterns as the water would experience going through elbows and turns in the water system. In small applications and/or very controlled circumstances the unit can be effective.

Another unit is the E.M.C. or electric-motor-charge unit. This unit is basically comprised of various metals that when placed apart at a maximum possible effective distance will cause a current to be generated across the space between the dissimilar metals. This type of unit operates in basically the same fashion as a magnetic unit, with one exception; the unit is allowing free electrons to enter the water and be taken up by the charged particles which are passing through the unit. Hence, this unit is somewhat more effective than the standard magnet unit, but only in a limited manner. Unfortunately, this unit is subject to being rendered ineffective by the accumulation of scale on the inside of the unit.

A third type of unit places two (or more) dissimilar metals at proper distances apart and uses an earth ground line to draw electrons in a fluid being treated as a result of the charge that is being exhibited by the metals within the unit. In this type of unit, the charge potential (number of available electrons in this case), is limited by the potential flow between the two dissimilar metals. Therefore, the unit will plateau out and become ineffective after a period of time.

U.S. Pat. No. 5,326,446 to Binger discloses an apparatus for treating fluids, in particular water, with static electromagnetic fields so as to purify the water by precipitating particulates and killing microbes. The circuit described in the Binger '446 Patent uses a power transistor to oscillate a low voltage iron core transformer at a broad range of radio frequencies. At particular intervals in the generation of these radio frequencies, the electromagnetic fields and waves reinforce each other and create high voltage spikes in the range of 100 to 10,000 volts and at frequencies from 10 cycles per second to several thousand cycles per second. The apparatus disclosed in the Binger '446 Patent can form a first high voltage static electromagnetic field, a second low frequency electromagnetic field, a third high frequency electromagnetic field and fourth radio frequency electromagnetic field. These low frequency, high voltage pulses in combination with the underlying radio frequencies induce the formation of negative ions within the water as a result. The negative ions tend to attach to the impurities, providing them with the necessary electrons to prevent the normal reactions to take place that would bring about scale for example. In the same manner, the negative ions can be used to split apart scale that has already formed thus eliminating scale that is already present. The apparatuses of the Binger '446 Patent does not provide controlled radio frequency (Rf) or signals or controlled synchronization of the voltage spike and Rf signals. While Binger discloses the utility of electromagnetically treated water for removing scale, Binger does not disclose or suggest that the treated water will provide a measurable benefit to living organisms such as plants and animals.

U.S. Pat. No. 3,753,886 to Myers discloses an apparatus for treating fluids with a controlled amount of alternating electrical current. The Myers '886 Patent discloses that the apparatus destroys all forms of plant and animal life contained in a fluid treated by the apparatus. Myers does not disclose that the treated fluids will provide a measurable benefit to plants or animals treated with, exposed to or consuming the treated fluids.

A wide range of other apparatuses for treating fluids or gases with an electromagnetic or electrostatic field are disclosed in U.S. Pat. No. 4,024,047 to Clark et al., U.S. Pat. No. 4,073,712 to Means, et al., U.S. Pat. No. 4,419,206 to Frame, U.S. Pat. No. 4,451,341 to Miller, U.S. Pat. No. 4,579,640 to Eades, U.S. Pat. No. 4,719,018 to Przybylski, No. 4,822,472 to Eris, et al., U.S. Pat. No. 4,871,450 to Goodrich, et al., U.S. Pat. No. 4,886,593 to Gibbs, U.S. Pat. No. 4,902,390 to Arnesen, U.S Pat. No. 5,106,495 to Hughes, U.S. Pat. No. 5,435,894 to Hayakawa, U.S. Pat. No. 5,447,626 to Ido, U.S. Pat. No. 5,792,247 to Browitt, U.S. Pat. No. 5,591,317 to Pits Jr., U.S. Pat. No. 5,567,293 to Paleologou, et al., U.S. Pat. No. 5,264,102 to Eibl, U.S. Pat. No. 4,704,983 to Bakke, U.S. Pat. No. 4,072,477 to Hanson, et al., and U.S. Pat. No. 4,012,310 to Clark et al. None of the above mentioned patent references either suggest or disclose the improved apparatus or methods of the present invention.

While it is true that many apparatuses for the electrostatic treatment of water are known and that such water can be consumed, the water treated with the improved electrostatic apparatus of the invention provides benefits which are measurably better than those benefits provided by other known apparatuses.

A large number of commercial and industrial fields employ fluids, in particular water-based fluids, and improvements in those fields are continually being pursued. Such fields include: horticulture, aquaculture, agriculture, manufacturing, health, production.

SUMMARY OF THE INVENTION

The present invention relates to improved apparatuses for electrostatically and/or electromagnetically treating fluids and to methods of using those treated fluids. One aspect of the invention provides an improvement in an electrostatic apparatus of the type comprising: a fluid conduit and a voltage spike signal generator, the improvement comprising:

including in the apparatus one or more radio frequency signal generators which cause the apparatus to emit at least two different controlled radio frequency signals;

including one or more antennas to form an antenna array for emitting said at least two different radio frequency signals and said voltage spike into said fluid conduit; and optionally tuning said radio frequency generators to provide a combination signal comprising a voltage spike signal and said two or more radio frequency signals having respective intensities;

wherein, the apparatus converts a source fluid to an energized fluid carrying a negative charge as the source fluid passes through said fluid conduit, and the energized fluid can provide a benefit to at least one of a living organism, process, apparatus, object, and device.

Another aspect of the invention provides an electrostatic apparatus for converting a source fluid to an energized fluid carrying a negative charge, the apparatus comprising:

a fluid conduit;

one or more antennas disposed in said fluid conduit for emitting into a source fluid a combination signal comprising a voltage spike signal and two or more radio frequency signals;

a voltage spike generator conductively connected to said one or more antennas for generating a voltage spike signal; and first and second radio frequency signal generators conductively connected to said voltage spike signal generator and said one or more antennas, for receiving said voltage spike signal and generating two or more controlled and different radio frequency signals;

wherein said voltage spike signal and said two or more radio frequency signals form a combination signal emitted by said one or more antennas into a source fluid to form an energized fluid carrying a negative charge.

The apparatuses of the invention can include one or more of the following:

1) a first component for dividing said voltage spike signal;

2) a second component for combining a first combination sub-signal from a first radio frequency signal generator with a second combination sub-signal from a second radio frequency signal generator;

3) a signal booster for amplifying or boosting one or more of the voltage spike signal, the two or more radio frequency signals, and the combination signal; and 4) a housing containing some or all of the electronic components of the apparatus.

The Rf signal generators can be adapted to create two, three, four or more distinct Rf signals having respective ranges and pulse widths. The Rf signal generators, signal booster(s) and/or antenna can cooperate to provide an improved electrostatic apparatus useful in particular applications.

Another aspect of the invention includes a method of using an energized fluid prepared with an improved electrostatic device according to the present invention. The energized water is capable of providing measurable benefits to all types of life forms, fluids, objects and processes. Accordingly, in another aspect, the invention is a method of measurably improving an aspect of or providing a benefit to a life form, fluid, object, or process comprising the steps of: treating a source fluid with an improved electrostatic apparatus to form an energized fluid bearing a negative charge, said improved electrostatic apparatus being adapted to subject said source fluid to a combination signal comprising a voltage spike signal and two or more controlled Rf signals having different radio frequencies; and subjecting at least one of said life form, fluid, object, and process to said energized fluid to provide a measurable improvement in an aspect of said at least one of said life form, fluid, object and process.

The life forms or living organisms which can obtain a measurable benefit from the energized water prepared according to the invention can include plants, animals, worms, fresh water creatures, and salt water creatures. The source fluid can include any known fluid but will preferably include water, water-based fluids, organic fluids. The source fluid can be a solution, suspension, emulsion, colloid, gel, or other such fluid. The object subjected to the energized fluid can include any object which can be associated with a fluid during use, manufacture, storage, transportation, relocation, and identification of the object. The benefit provided by the improved apparatus of the invention will be measurably better than any benefit provided by known electrostatic apparatuses.

Exemplary benefits provided by the treated fluid include: improved crop yield, improved pest resistance in crops, improved crop health, increased milk production in dairy cattle, improvement in animal health, improved resistance of animals to disease and infection, increased growth rates and production rates in plants and animals, improved octane rating of standard petroleum based fuels, reduction in pollutant formation during combustion of fuels, reduced drying time for concrete and cement, reduction in perceived bitterness in juice, reduction in scale formation and build-up in fluid conduits, improved sterilization of water having high microbial content, enhancement of flavor in drink syrup or concentrate, improved crop grass growth and condition, increased crop productivity, increased water percolation into soil, increased efficacy of fertilizers and nutrients, improved plant drought tolerance, improved leaching of salts into subsoil, algae control, and enhanced efficacy of medicines.

BRIEF DESCRIPTION OF THE DRAWINGS

For a more complete understanding of the present invention, and for further details and advantages thereof, reference is now made to the following Detailed Description taken in conjunction with the accompanying drawings, in which:

FIG. 1 is a schematic of a commercially available prior art electrostatic discharge unit which does not include the improvements of the invention;

FIG. 2a is a graphic representation of one embodiment of the voltage spike signal generated by the circuit of FIG. 1;

FIG. 2b is a three dimensional graph of the combined static electromagnetic signal and the uncontrolled and varying radio frequency electromagnetic field signal which is generated by the circuit of FIG. 1;

FIG. 3a is a partial cross sectional side elevation view of the apparatus according to the invention;

FIG. 3b is a sectional end view of the apparatus of FIG. 3a along lines 3b—3b;

FIG. 7b is a first combination sub-signal generated by an Rf signal generator having received the voltage spike signal of FIG. 7a;

FIG. 7c is a second combination sub-signal generated by a second Rf signal generator having received the voltage spike signal of FIG. 7a;

FIG. 7d is a graph of a third combination sub-signal generated by a third Rf signal generator having received the voltage spike signal of FIG. 7a;

FIG. 7e is a fourth combination sub-signal generated by a fourth Rf signal generator having received the voltage spike signal of FIG. 7a;

DETAILED DESCRIPTION OF THE INVENTION

Figure 4:
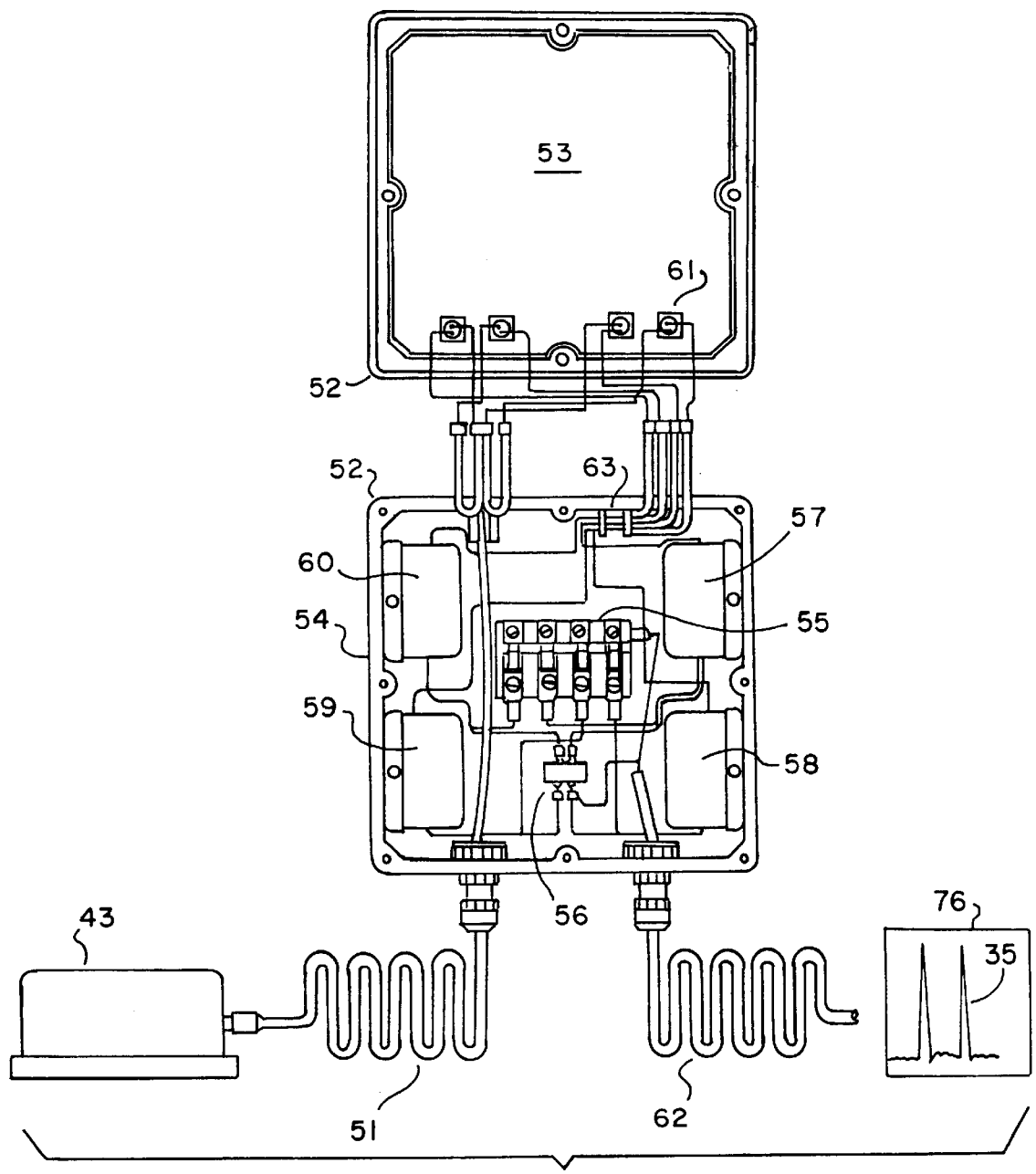
FIG. 4 is a top plan view of the electronic components of the apparatus according to the invention.

FIG. 1 is a schematic of some of the electronic components in the device disclosed in U.S. Pat. No. 5,326,446, the entire disclosure of which is incorporated by reference. The embodiment of FIG. 1 does not include the improvements according to the invention. The electrostatic device's primary components include a step down transformer (12), an oscillating transistor (18), and a step up transformer (22). A standard 115 volt AC power supply is connected across the terminals (10a) and (10b) at the input of the circuitry. The power supply powers the primary winding (12a) of the step down transformer (12). The step down transformer (12) has a secondary winding that provides a voltage range which is then provided to the center tap (22a) of the step up transformer (22) by way of the diode (14). The combination of the transformer (18) and the step up transformer (22) creates an oscillator that creates a wave form static electomagnetic low frequency pulse combination signal (35) formed by the random synchronization of a voltage spike with a plurality of underlying radio frequency signals of varying voltage. (See FIG. 2a). In combination, this power circuit provides random radio frequency oscillations or signals at the output of the step up transformer (22). The pulse signal (35) is conditioned by the diode (24) and the capacitor (26) to provide a combined radio frequency signal across the terminals (28) and (30) that are connected to the electrodes.

Operation of the above described circuitry creates a wave form or combination signal (35) similar to that shown in FIG. 2a. The reference base line shown in FIG. 2a may be any DC offset desirable for the particular application involved. Referring now to FIG. 2b, the combination signal (35) comprises a combination of radio frequency (signals (36), 37, 38) which are created periodically. The combination signal which can be of up to 2,000 volts or more results from the intermittent positive reinforcement of a voltage spike signal with the underlying radio frequencies. The combination signal (35) provides a low frequency signal necessary for certain types of water purification. At the same time, the underlying radio frequency signals (36, 37, 38) in the pulse signal (35) provide the necessary electromagnetic field fluctuations which eliminate or reduce potentially harmful components in a fluid being treated.

The pulse width of the combination signal (35) described in FIG. 2a is approximately 10 microseconds. The pulse width, however, can be controlled by appropriate adjustment of the biasing of transistor (18) shown in FIG. 1. All of the characteristics of the combination signal (35) shown in FIG. 2a can be modified by appropriate biasing and resistance and capacitance change to the circuitry in FIG. 1. The resistor (20), for example, can be replaced by a variable resistor (not shown) which would allow a user to modify the output signal. The only critical characteristics of the combination signal (35) are the inclusion of its underlying radio frequency signals (36, 37, 38), its low frequency pulse structure, the high voltage level of the pulse and the short pulse widths of the pulses. It is the combination of all of these wave elements that creates the versatility of the circuitry to drive electrodes in a number of different applications.

Referring again to FIG. 2b, it will be understood that the voltage of a pulse signal or voltage spike of the combination signal (35) can be varied as desired and that the frequency of the combination pulse signal (35) will generally be a low frequency as compared to the radio frequency of the underlying signals (36), (37), and (38). In its simplest embodiment, the combination signal (35) will comprise 2, 3, 4 or more underlying radio frequency signals creating a varying electromagnetic field. The radio frequency signals (36), (37), (38) can have different respective frequencies as well as different respective voltages according to the intended use of the apparatus of the invention. The present invention includes electronic components which are intended to modify and control the frequency, periodicity and amplitude of the radio frequency signals emitted by the apparatus of the invention. Such electronic components are described below.

The unimproved device depicted in FIG. 1 was designed for use in treating water and in particular for the removal of scale and bacteria from the water as described in the Binger '446 Patent. However, the present inventor has discovered that all types of fluids, and in particular water, which have been energized with the prior art device can provide a marginal benefit to some living organisms and apparatuses. The present inventor has also discovered that incorporation of the improvements of the present invention into any type of voltage spike generating apparatus as described further will create a device capable of forming an energized fluid which provides a significant and measurable benefit to many living organisms, objects, equipment, processes and the like.

FIG. 3a is a partial sectional perspective view of a portion of an electrostatic device according to the invention which comprises a fluid conduit (50) having opposing ends (46), a signal booster (43) engaged with the fluid conduit (50), and one or more antennas (44) disposed within the cavity (45) of the conduit (50). The device can be engaged with pipes (40) and (42) to direct the entry and exist of fluid through the device.

FIG. 3b is an end view of the partial device depicted in FIG. 3a. The three antennas (44) are affixed to a support comprising a support ring (48) and a support rod (47) which is conductively connected with the signal booster (43) such that the final combination signal from the signal booster (43) is passed on to the supporting rod (47). The signal received by the supporting wire (47) is then passed on to the antennas (44) by way of the support rings (48). As fluid passes through the passageway (45), it is exposed to a combination signal comprising a static electromagnetic voltage spike or pulse in combination with two or more predetermined and controlled radio frequency signals.

FIG. 4 is a top plan view of the electronic components comprised in the improved device of the invention. In operation, an electrostatic signal generator (76) generates plural low frequency voltage spikes (35) which are conducted to components in the component box (52) by way of the conductor (62). The conductor (62) conducts the voltage spikes (35) to first and second buses, (55) and (56), respectively, the bus (55) comprising one or more fuses or fusible links. In the present embodiment, the voltage spike signal (35) is split by the bus (55) and is then conducted substantially simultaneously to first (57), second (58), third (59), and fourth (60) Rf signal generators, each of which forms a respective combination subsignal comprising a voltage spike and one or more controlled and predetermined radio frequency signals. The combination subsignals are then combined by the bus (56) with a portion the original voltage spike (35) to form a final combination signal which is conducted to the signal booster (43) by way of a conductor (51). The final combination signal that has been boosted by the booster (43) will be conducted to one or more antennas (not shown) and transmitted directly into a fluid being treated by the apparatus of the invention.

While FIG. 4 depicts an embodiment where the source voltage spike (35) is split and conducted substantially simultaneously to plural Rf signal generators (57–60), the present invention includes embodiments where the voltage spike signal (35) is modified as follows. The voltage spike signal (35) is conducted by way of the conductor (62) to a first bus and a first Rf signal generator. The first Rf signal generator adds to the voltage spike an underlying Rf signal having a predetermined frequency to form a first combination sub-signal. The first combination sub-signal is then conducted, either serially or in parallel, to one or more other Rf signal generators that add additional Rf signals to the first combination sub-signal to create second, third, or fourth combination sub-signals comprising a first voltage spike signal and two or more different Rf signals. The combination sub-signal received from the last Rf signal generator is then combined with a portion of the voltage spike (35) to form a final combination signal which is conducted through an optional signal booster to one or more antennas which transmit the final combination signal directly into a fluid being treated.

Figure 5:
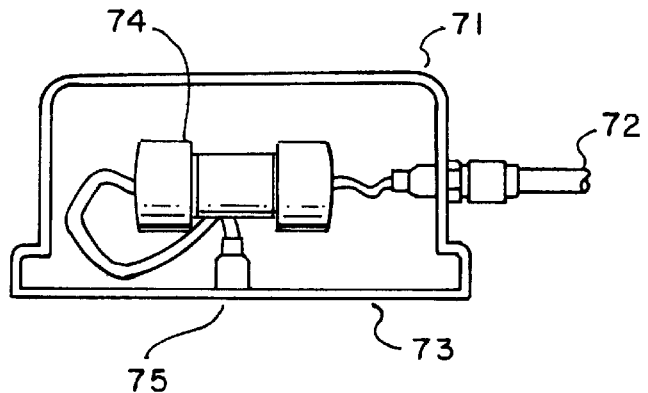
FIG. 5 is a sectional side elevation view of a signal booster according to the invention.

A signal booster (43) according to the invention is adapted to increase the voltage or amplitude of one or more of the final combination signals, the voltage spike signal (35), or the underlying Rf signals. The signal booster (71) depicted in FIG. 5 comprises a housing (73) and an electronic signal booster (74) which is coupled to the circuitry of the component box (52) by way of the conductor (72) and which is further coupled to one or more of the antennas (44) and the device (41).

Referring again to FIGS. 3 and 3(b), the device can comprise one or more antennas (44). The number of antennas (44) and their disposition within the passageway (45) can be optimized for particular applications as desired. As described in the tables and examples below, a first antenna array comprising one or more antennas (44) will be suitable for a first application while a second antenna array comprising one or more antennas (44) will be suitable for a second application. It will be understood by those of skill in the art that any material which is known to be suitable for the emission or transmission of Rf signals and voltage spikes into a fluid will be suitable for the device of the invention.

Referring again to FIG. 4, the component box (52) can comprise two or more Rf signal generators each of which generate one or more Rf signals having a predetermined and controlled frequency and optionally a pre-determined amplitude or voltage. As used herein, the term "Rf frequency generator" which describes the components (57) through (60) is taken to mean an electronic component capable of creating an Rf signal when a voltage spike is received by the component. An Rf signal generator will also be able to conduct the source voltage spike (35) along with the Rf signal that the component generates. It will be understood by those of ordinary skill in the art that almost any known Rf signal generator can be used. It is only necessary that the Rf signal generator be able to generate an Rf signal having a predetermined and controlled frequency.

The one or more indicators (61) depicted in the lid (53) of the component box (52) can include any indicating means known to the those of ordinary skill. For example, the indicator (61) can include a light bulb, LED, sound generator, vibrator or other indication means which are activated by an electrical current.

It will be understood by those of ordinary skill in the art that various combinations of two or more Rf signal generators and one or more antennas and/or one or more signal boosters can be used to prepare energized fluid having the properties described herein.

As used herein, the terms "voltage spike generator" or "pulse generator" refer to an electronic device capable of generating a voltage spike which will be conducted through the circuitry of the presently claimed device and ultimately transmitted to a fluid being treated by the device. Any of a number of commercially available devices are suitable for formation of the voltage spike which serves as a basis of the final combination signal. Such voltage spike generators include an electrical generator, a charged capacitor, and a staodyn portable pulse generator. Specific voltage spike generators include the Silver T and Silver T slimline devices of Concepts 2000, a hydromax or electronic control device, the solar pulse generator of Speedrite, the hot-wire or electrical fence device of Pel which operates at 110 volts, the Model SM2000 of Speedrite which operates at 220 volts, the pulse generator Series TG of Ritter, the regulated adapter of Go, and the 500 MA Model 273-1652D of Radio Shack, where the Go and Radio Shack devices can be used with an IDI neon lamp Model 211082 to generate the voltage spike.

As used herein, the term "signal booster" refers to one or more electronic components that amplify the magnitude or voltage of a signal generated by the presently claimed device. The signal booster can modify one or more of the final combination signal, the one or more underlying Rf signals and the voltage spike signal. A signal booster can be made from commercially available materials such as wires, magnets, copper fittings, etc. It will be understood that a wide variety of signal boosters can be used, and such boosters include the Model CR66 booster of Pyramid, the Model FX5A booster of Autotek, the Model 151118B signal amplifier of Radio Shack, the Model 151115B booster of Radio Shack, the Optimus Signal A Model 12-2018 booster of Radio Shack, the Optimus 50 booster Model 121970 of Radio Shack, the Model AR00001 amplifier of Uplinx and the crossover booster Model XB212 of Pyle.

The Rf signal generators according to the invention will be capable of generating a radio frequency signal when a voltage spike is passed through it. Different Rf signal generators will generate different Rf signals, and such signals can be combined to provide specific benefits in different applications. The Rf signal generators will comprise conventional components such as resistors, capacitors, transformers, diodes, and other electronic components known to those of skill in the art. The Rf combination signals generated by the Rf generators can be independently or simultaneously controlled and tuned so as to provide a desired final combination signal comprising two or more Rf signals and a voltage spike signal.

Figure 7A:
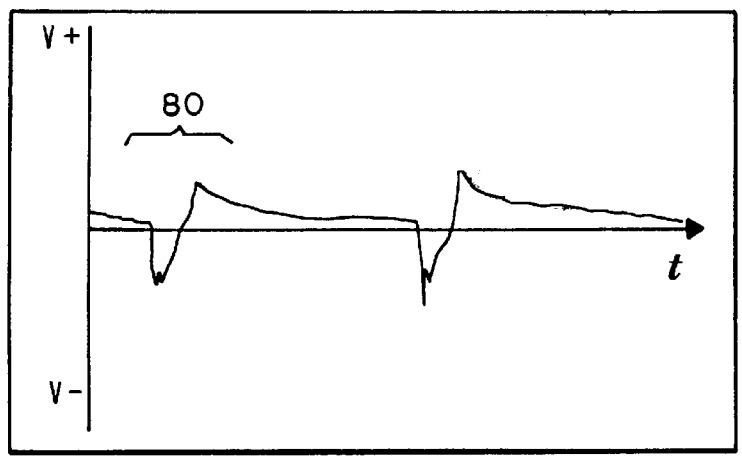
FIG. 7a is a graph of a voltage spike signal generated by a voltage spike signal generator.

In one exemplary embodiment, the device according to the invention can comprise a voltage spike generator, such as a 12 volt adapter sold by Radio Shack, and a Neon light wherein the ground lead of the adapter is grounded and a Neon light, which serves both as a conductor and a resistor, is put in line with the adapter. The voltage spike (80) generated by the circuitry is depicted in FIG. 7a. The voltage spike (80), at this point, has not been conducted through any of the Rf signal generators included in the device of the invention.

Figure 7B:
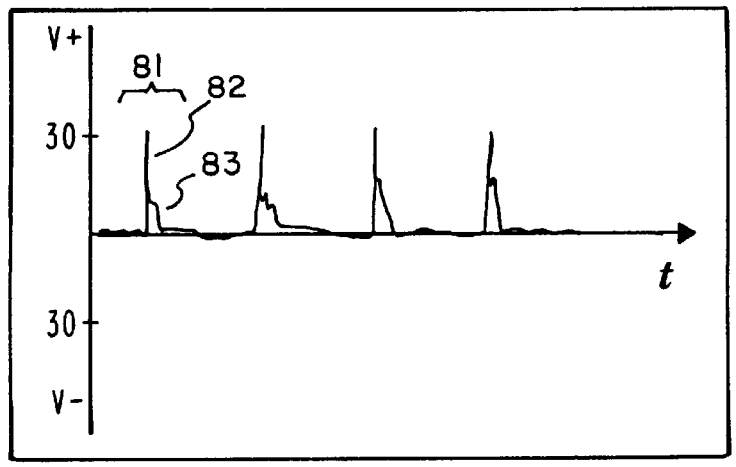

FIG. 7b depicts a first combination subsignal (81) which comprises a voltage spike (82) and two underlying Rf signals (83). The combination subsignal (81) is formed by the Rf signal generator (57) after it has received a voltage spike. The Rf signals (83) have known and controlled radio frequencies, and in a preferred embodiment, they will occur a brief period of time after the peak of the voltage spike (82).

Figure 7C:
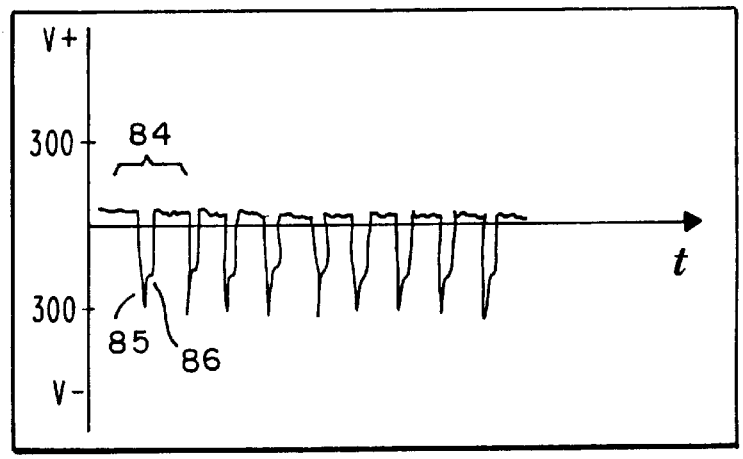

FIG. 7c depicts a second combination subsignal formed by the Rf signal generator (58) after it has received a voltage spike signal (80). The signal (84) has a negative overall voltage and comprises a negative voltage spike (85) and two underlying Rf signals (86) having a negative voltage as well. The second combination subsignal (84) is offset in time with respect to the signal (81) such that the signals (81) and (85) do not cancel each other out.

Figure 7D:
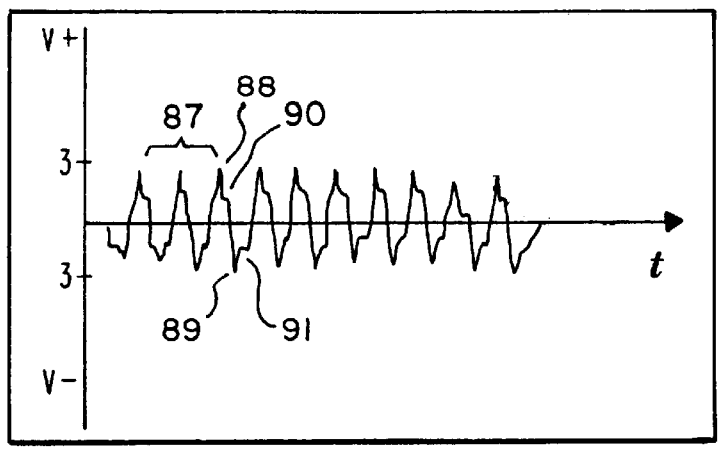

FIG. 7d depicts a third combination subsignal (89) formed by the Rf signal generator (59) after it has received the voltage spike signal (80). The signal (87) comprises the positive voltage spike (88), the negative voltage spike (89), the positive Rf signals (90) and the negative Rf signals (91). The combination subsignal (87) formed by the device has both a positive and negative voltage component. The Rf signal generator (59) comprises a signal splitter, a signal inverter, and an Rf signal generating means.

Figure 7E:
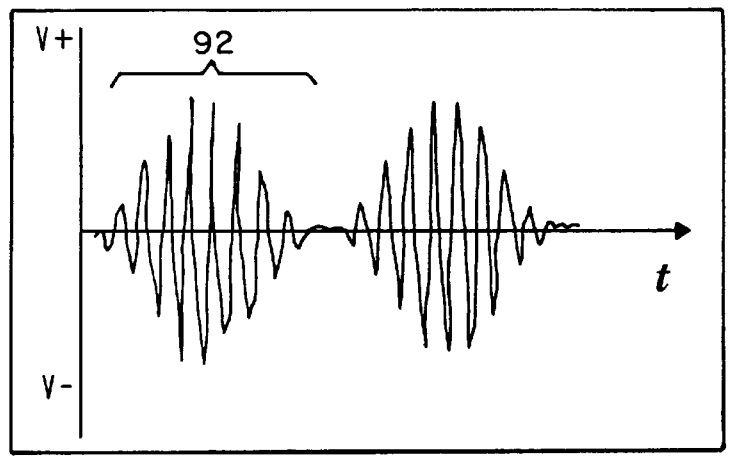

FIG. 7e depicts a fourth combination subsignal (92) formed by the Rf signal generator (60) after it has received the voltage spike (80). The signal (92) comprises plural oscillating positive and negative voltage spikes and one or more underlying Rf signals wherein the plural signals as a group have an amplifying component and a decaying component.

Figure 7F:
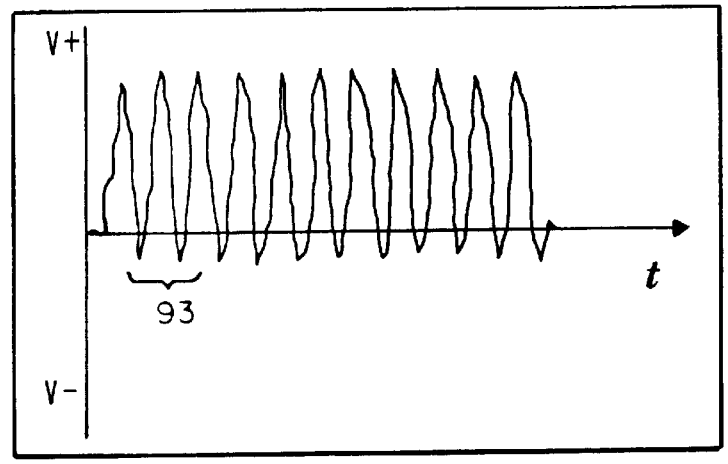
FIG. 7f is a final combination signal comprising the first, second, third and fourth combination sub-signals of FIGS. 7b, 7c, 7d and 7e wherein the final combination signal has been boosted with a signal booster according to the invention.

The final combination signal (93) depicted in FIG. 7f has been formed by the use of one voltage spike generator (76) and four Rf signal generators (57–60) as depicted in FIG. 4; however, the invention includes devices comprising a voltage spike generator, one or more Rf signal generators and optionally one or more signal boosters. The output signal of the various Rf frequency generators can be synchronized or harmonized so as to optimize the output signal (93) for particular applications. The synchronization can be done by adjusting the output signals (80), (81), (84), (87) and (92) such that their respective voltage spikes will overlap.

Figure 8:
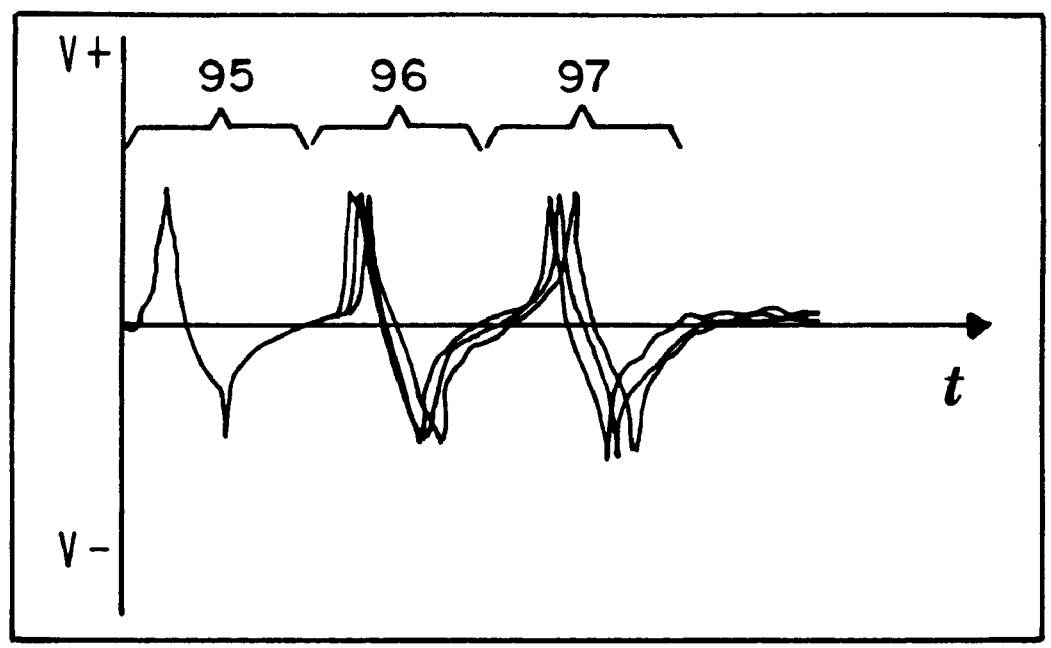
FIG. 8 is a graph depicting the result of synchronizing and a synchronizing the underlying combination signals of a final combination signal.

FIG. 8 depicts a graph showing the differences between synchronized spike and Rf signals (95), partially synchronized Rf and spike signals (96) and asynchronized spike and Rf signals (97). It will be understood by those of skills in the art that the synchronization of the spike and Rf signals can be affected by adjusting a setpot in one or more of the spike signal generator and the Rf signal generators. In the embodiment of FIGS. 7a–7f and FIG. 8, the voltage spike can be generated by a Neon lamp. It will be understood upon review of these figures that the final output signal (93) which is used to treat and energize a fluid can be further modified in voltage amplitude, wave form frequency, and radio frequency.

Since the presently claimed device requires two or more Rf signals and a voltage spike that can be synchronized, the synchronization of the signals can be used to provide unexpected benefits not available with prior art devices. For example, the presently claimed device can be used to kill or lyse E-coli cells which are resistant to an Rf signal of 802 KHz, the frequency typically used to lice these cells. These resistant E-coli cells can be killed by using several Rf signal generators together that have been harmonized or synchronized. As a further example, a device according to the invention which employs synchronized Rf and voltage spike signals can be used to attract fish in a pond by placement of the antenna of the device in the water and emission of the final combination signal generated by the device. In response to the output signal, the fish will draw nearer to the antenna.

An Rf signal generator will be capable of generating one or more Rf signals having a predetermined and controlled frequency after receipt of a voltage spike signal. An Rf signal generator will comprise an Rf signal generating means and can further comprise electronic components that alter the voltage spike received by the generator. For example, a first Rf signal generator can add at least two different Rf signals to a voltage spike. A second Rf signal generator can invert the polarity of a voltage spike and add at least two Rf signals to the voltage spike. A third Rf signal generator can split a voltage spike into two sub-spikes, the first sub-spike having a positive polarity and the second sub-spike having a negative polarity with a greater amplitude than the first subspike and can also add at least two Rf signals to the voltage spikes. A fourth Rf signal generator can split the voltage spike into two or more sub-spikes having opposite polarity and can add Rf signals to one or more of the sub-spikes such that Rf signals of positive and negative polarity are generated. A fifth Rf signal generator can convert a single voltage spike into at least eight different voltage sub-spikes by first having a positive polarity and the second half of the sub-spikes having a negative polarity, wherein the subspikes that most closely approximate the peak of the first voltage spike have a greater amplitude than those sub-spikes that are more removed from the peak of the first voltage spike. Accordingly, an Rf signal generator, according to the invention, can comprise an Rf signal generating means and optionally one or more of a voltage spike signal splitter, a voltage spike signal inverter, a voltage spike signal amplifier, a voltage spike signal multiplier and a voltage spike signal dampener.

In the embodiment of FIGS. 7a–7f and 8, the device of the invention comprises first and second buses, a first bus of which disseminates a first voltage spike to each of one or more Rf frequency generators and the second bus of which receives and combines plural combination sub-signals received from each one of one or more Rf signal generators according to the invention. Accordingly, the electronic components and the improved device of the invention can be adapted to simultaneously or in parallel alter a voltage spike signal received from a first bus or to sequentially or serially alter signals received from a voltage spike generator or one or more other Rf signal generators.

As used herein, the term "energized fluid" refers to a fluid that has been treated with a device according to the invention and which possesses a measurable electrostatic potential or negative charge as determined by a voltmeter. For example, a source fluid having a millivolt reading of zero to −10 millivolts can be treated with the claimed device to form an energized fluid having a millivolt reading of −10 to −100 millivolts. Although it is not clearly understood at this time, it is believed that the negative potential which resides in the energized fluid is due to electrons, negative ions, or other negatively charged atomic or molecular species formed in the fluid by an improved device of the invention. Without the improvements of the invention, prior electrostatic devices used to create energized fluids possessing a negative potential which dissipates rapidly upon discontinuation of the treatment. In contrast, when a source fluid is converted to an energized fluid with the improved device of the invention, the measurable electrostatic potential will continue to exist well beyond the point at which the device is turned off. In one embodiment, the electrostatic potential will continue to reside in the energized fluid for a period of at least one day, preferably at least three days, more preferably at least seven days, even more preferably at least two weeks, yet even more preferably at least one month and most preferably at least two months after the point at which the device is turned off.

Figure 6:
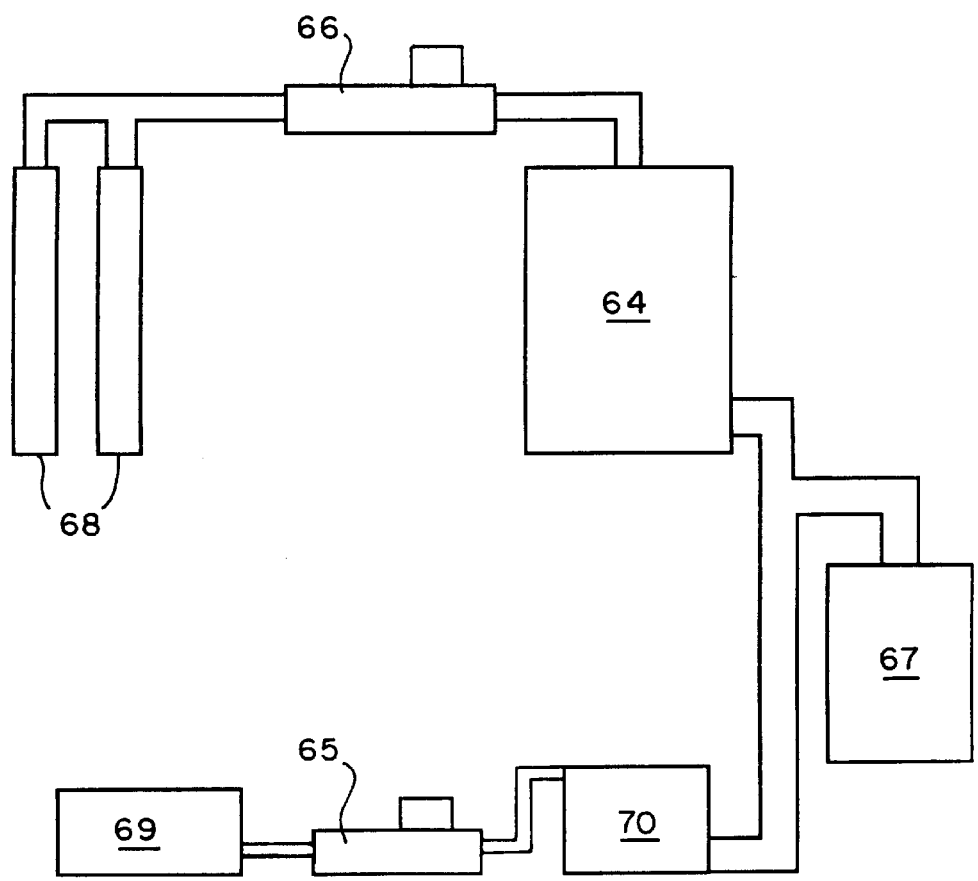
FIG. 6 is a flow diagram for the preparation of energized juice prepared with the apparatus of the invention.

FIG. 6 depicts an industrial application of the present device for the preparation of aloe vera juice. Aloe vera juice is derived from the aloe vera plant and typically has an undesirable, bitter flavor. It has now been determined that the present device is useful for reducing or eliminating the bitter flavor in aloe vera juice. An exemplary process follows. The aloe vera concentrate is stored in a flat tank (69). Commercially available water is stored in second tanks (68). A first electrostatic device (66) of the invention is placed in series between the second tanks (68) and the first receiving tank (69). Water is then pumped through the electrostatic unit (64) and stored in the tank (69). A second electrostatic device (65) is placed between the first tank (60) and a second receiving tank (70). The aloe extract in the tank (69) is treated with the device (65), and the energized aloe extract is placed in the second receiving tank (70). The energized solutions are then mixed and stored in a finished product tank (67). The resulting energized mixture is no longer bitter. Further, consumers attest to feeling better and healthier after drinking the treated aloe vera juice, and the treated juice has a longer shelf life.

It is not necessary to energize both the water diluent and the juice extract. An energized water diluent can be combined with aloe vera juice and other healthful juices to form energized juices. When mixed with energized water, juices generally lose much of their bitterness and appear to provide their users with more energy.

It will be understood that the present application is not limited to aloe vera juice. Similar results have been achieved with all fruit and vegetable juices, including, but not limited to, cranberry juice. Similar results have also been achieved with tea and colas, carbonated and noncarbonated drinks, and sweetened or unsweetened drinks. Generally, after the water or liquid food product is treated, it has a measurable increase in energy levels as determined by a voltmeter.

Human, Animal and Plant Applications

The benefits provided by energized fluids to humans, animals and plants are numerous. Animals and plants consuming energized water have demonstrated extended life, improved health, and improved production. For example, after consuming energized water, in particular energized water from the improved device, chickens will lay more eggs; cattle will provide more consumable meat per head; dairy cattle will produce more milk per head; and shrimp production in a nursery will be increased. A cow should ingest between 1–300+ pounds of energized water, depending on desired milk production. If a human ingests the normal amount of water taken consumed by the average human during the course of a day, and the water has been treated by an improved device of the invention, the individual's general health, and resistance to disease can improve over time.

With regard to plants, farmers generally experience a higher crop yield when they treat their crops with the energized water of the invention. Moreover, the crops are generally healthier and ready for harvest sooner than normal. The sugar or brick count of a plant is normally looked at to decide the quality of a crop plant. In the case of plants treated with the present device, the brick counts are almost always larger than if the plants had not been treated with the energized water. After harvest, there is generally less spoilage of the harvested crop during handling and shipping. The final products also have an extended shelf life. For example, if a farmer irrigates a field with water containing between 25% and 100% of the energized water, he will experience results generally exceeding his present production. Use of treated water also allows farmers to produce on land not previously used because of salt and/or other contaminants.

In cotton farming, there is increased cotton production, increased cotton bowl maturation, and a decrease in cotton lock when energized water is used to irrigate the cotton plant. The treated water can also remove scale in a cotton gin and prevent it from reforming.

In the field forestry, trees watered with the treated water have shown greater stability and survival in seedlings for planting, reduced water requirements for same amount of growth and accelerated reforestation. The same holds true in the regular plant nurseries. Because the crops are healthier, secondary benefits also arise: farmers can decrease their use of pesticides, herbicides, and fertilizers. All of these benefits also apply to non-farming applications such as residential landscaping and on golf courses.

Energized water made with the improved device of the invention can be used to increase silage in crop plants. For example, barley silage production can be increased dramatically with respect to control by irrigating a barley field with energized water made with the improved device of the invention. In one particular example, the barley silage production increased 72% over control by irrigating the barley with water treated by the improved device of the invention, where the control is water-treated with the unimproved device as disclosed in the Binger '466 Patent. (See Example No. 7.)

Feed grasses such as Rhodes grass, which is commonly used to feed livestock, can be improved by irrigation with energized water made with the improved device of the invention. For example, when Rhodes grass was treated with energized water made with the unimproved device, the oxygen content was 1.8% and the total protein content was 11.25%; however, when energized water made with the improved device of the invention was used to irrigate the Rhodes grass, the nitrogen content was raised to 2.6% and the protein content was raised to 16.25%. Accordingly, the improved device of the invention can be used to increase the feed value of feed grasses. Another example, alfalfa which is another feed grass, was treated with energized water made with the unimproved device of the invention. The control alfalfa had a moisture content of 56.08%, a protein content of 19.53 and a crude fiber content of 31.49. In comparison, alfalfa treated with energized water made with the improved device of the invention had a moisture content of 80.6%, a protein content of 25.3%, and a fiber content of 22.6%. It will be understood by those of skill in the art that the increased protein content and reduced fiber content are properties which are desirable to the cattle industry since higher protein and lower fiber content results in an easier to digest grass which is more nutritious for cattle. (See example 8.) It will be further understood that the above values can sum greater than 100% as they have been determined independently of one another.

Additional applications of the energized water made with the improved device of the invention have been demonstrated in various fields as follows:

1. Poultry industry—reduction of chicken mortality and chicken sickness rate, increased tolerance to disease, increased selling rates, reduced number of days to achieve selling weight;
2. Strawberry industry—reduced demand for irrigation water, improved plant and fruit quality, increased fruit production, superior keeping quality;
3. Nursery grown roses (with regard to the growth and production of roses in a hydroponics greenhouse operation)—reduced fertilizer requirement, simplified plant care, improved plant figure and strength, increased flower production, increased flower size;
4. Tomatoes and grasses production—improved germination of seeds up to 100%, earlier rooting of plant cuttings, increased sod growth with reduced water demand, improved plant resistance to pests such as insects and viruses, reduced demand for pesticides, increased production, increased tomato size; and
5. Crop trees—increased number of blooms and fruits per tree.

The previous benefits detailed above have also been obtained with plants such as poinsettias, callalillies, sunflowers, pansies, grapes, dates, and vegetable plants such as broccoli, cauliflower, onion, celery, green pepper, tomato, lettuce, cabbage, squash, cucumbers, vegetable plants, fruit plants, corn, lentils, green beans, lettuce, sun flowers, beaugainvillaea, orchids, carrots potatoes, peanuts, petunias and others.

While particular applications will require a particular combination of Rf signal generators, antenna array and optional signal boosters, the following general trends have been observed. In applications concerning animals such as chickens, cows, or horses, it is generally preferred that the improved device of the invention incorporate at least two Rf signal generators. It will be necessary, however, to select the proper frequencies for the Rf signal and to synchronize the Rf signals and electrostatic voltage spike signal as described previously. It has been observed that particular applications such as, for example, increasing egg production in laying hens or increasing chicken size in broiler chickens, will require a different combination and range of Rf signals than would be required to increase weight in beef cattle or increase milk production in dairy cattle. It will be understood by those of skill in the art that contaminants in the water might affect the efficacy of the energized water. Accordingly, an analysis of the source water prior to treatment with the improved device of the invention should be conducted to identify such contaminants so that the improved device can be modified to account for the presence of those contaminants and still provide the intended benefit.

An improved device having at least three Rf signal generators would typically be required for agricultural applications such as improvement in the nutritional value or quality of feed grasses and crops, improvement in flower production in greenhouse nurseries, increase in edible fruit and vegetable production and the like. The improved device having at least three different Rf signal generators would generally be suitable for agricultural applications wherein a farmer already has the soil in proper condition for optimal growth and as such the energized water will be used to maintain the soil in optimal condition, reduce the demand for herbicides and pesticides, and reduce the demand for fertilizers. In agriculture applications where a new crop is being introduced into a field or a field is not a proper or optimal growing conditions, an improved device with the invention would generally comprise at least four different Rf signal generators. The fourth Rf signal generator will typically transmit frequencies that cannot be tolerated by most insects and also improve a crop's overall pest resistance. Accordingly, an improved device comprising four Rf signal generators will not only increase the nutritional value of a crop but will also improve a crop plant's overall health, increase the crop plant's pest resistance, and ward off or significantly reduce insect infestations.

Water treated with the improved device of the invention has also be found to be useful at increasing the production of, increasing the survival rate of, reducing the feed requirement of and reducing the time-to-market of nursery grown shrimp. (See Example 9)

Medical and Dental Applications

Energized water prepared according to the invention can be used to more effectively clean instruments and equipment such as a dialysis machine. For example, since the water can be made free of it's contaminants using an improved device, flowing the water over an instrument for a sufficient length of time will cleanse the instrument. Many of the parts of a dialysis machine must be cleaned between uses. Washing the unit parts with a stream of the treated water can cleanse the parts and the higher electron charges helps to precipitate microscopic particles from the surface of these parts, similar to removing the scale from the inside of the pipes and then keeping it from building up again. Thus, the improved device can be used as a means of lowering the required dosages of medication to be administered while still providing the same therapeutic effects.

Vitamin and Mineral Applications

Energized fluid prepared according to the present invention can be used in the field of nutrition, in particular, for being combined with vitamins and minerals to minimize unwanted reactions between vitamins and minerals, which reactions can cause the degradation of or a decrease in efficacy of the vitamins and minerals. The device of the invention and fluids treated therewith can help chelate minerals to facilitate there uptake by plants and animals, preserve minerals and vitamins by reducing degradation and unwanted reactions, and increase the efficacy of vitamin and/or mineral containing compositions.

Industrial Applications

Industrial applications for the treated water are abundant. In general, water that passes through a controlled electrostatic field in the improved device has an improved taste, is odor free, controls algae, can control bacteria, and is environmentally safe. The water from the unit is similar to the water from the water softener, in that users find that soaps lather better; they wash with less detergent and water spotting is reduced, without the addition of salt as in water softeners. Old scale will be removed from pipes and new scale will be prevented from forming without the use of costly chemicals.

There are many systems that require or are optimized by scale removal. Cooling towers, and boilers and other types of heat exchangers for example. As the amount of scale is reduced, the units run better, which in turn reduces fuel consumption and increases the units life. For swimming pools, the pool stays cleaner, and the use of chemical scale control is eliminated. Irrigation systems and small water spray heads also can clog with scale. Treatment of the water before it passes through the head of a sprayer will remove existing scale and prevent new scale from forming. Additionally, the high electron concentration in the water has demonstrated bacterial control, fungal/algae control, parasite control, and potential viral control.

Another surprising application for the energized water made with the improved device of the invention is in the reduction of drying time for cement and concrete. For example, when water which is treated by the electrostatic device of the Binger '466 Patent was used to make cement, the drying time for the cement was approximately 12 hours. However, when energized water made with the improved device invention was mixed with the cement, the cement drying time decreased to 3–4 hours. (See Example 1.)

The improved electrostatic fluid treating device of the invention is also applicable for the treatment of gasoline and other petroleum products. Prior to treatment with the improved device, a control gasoline was found to have an octane rating of 87%, and after treatment of the gasoline with an unimproved device, the octane rating was unchanged. However, when the gasoline was treated with the improved device of the present invention, the octane rating of the gas increased to 92%. The octane rating was determined according to the known D-2699 standardized method. (See Example 2.)

The improved device of the invention has also found use in the combustion of liquid byproducts in stacks. For example, the improved device of the invention was used in a combustion stack wherein the influent line containing the byproduct liquid stream was injected into the stack and combused therein. The influent fluid was treated with the improved device of the invention prior to entry into this stack. To control runs were conducted using untreated influent fluid and the ensuing stack temperature, carbon dioxide level in the exhaust, smoke in the exhaust, and flame color were determined. In a similar fashion, a test using fluid treated by the improved device of the invention was also conducted and the same parameters determined. It was determined that use of a treated influent stream allowed the stack to be run at 40° to 50° F. lower than the stack was run using the untreated fluid. Further, a lower level of carbon dioxide was emitted from the stack and the flame color using the treated fluid indicated a more efficient combustion of the influent than was observed when using the untreated fluid. (See Example 3.)

Industrial processes employing fluids typically require that the fluids be tracked as they course through fluid conduits into different parts of a processing system. In particular, some processes require that a first fluid in a first conduit be partitioned and directed into second and third fluid conduits according to the properties of the first fluid. For example, in the petroleum industry, the quality of crude oil from a single well or even within a single lot typically varies significantly. As the oil flows through a fluid conduit network, it is treated and analyzed at various points throughout the network and then partitioned from a first conduit into second and third conduits. Methods of tracking the oil through the network include, for example: 1) monitoring one or more properties of the treated oil such that when a property changes the oil is diverted from a first conduit into a second conduit; and 2) adding a chemical tracer to the oil at a first point in a first conduit and determining the presence of the tracer in the oil at a downstream second in the first conduit such that when the chemical tracer is detected in the oil, the oil will be diverted from the first conduit into a second or bypass conduit. It will be understood by those of skill in the art that the diversion of fluids within a conduit network is typically accomplished with a combination of quality control equipment, analytical equipment, valves, switches, detectors, computers and optionally other components and equipment.

It has now been discovered that the overall negative charge that the improved apparatus of the invention adds to fluids can be used in place of a chemical tracer to "mark" the fluid. For example, a suspension comprising crude oil and water is flowed through a first point of a fluid conduit network comprising oil treating equipment such as one or more oil additive injectors which inject different types of oil additives into the suspension according to the intended use of the suspension. Devices according to the invention are placed at points in the conduit substantially immediately downstream from the one or more injectors, such that when a first injector injects a first oil additive into the suspension a respective device according to the invention will begin to energize the treated suspension. At a second point farther downstream in the fluid conduit, a voltage detector detects the energized suspension containing the first oil additive, and the energized suspension is diverted to a second conduit until such time as the voltage detector no longer detects energized suspension and the unenergized suspension is diverted back to the first fluid conduit.

EXAMPLE 1

Cement Production

The use of energized water made by the unimproved device versus the improved device was evaluated in the production of cement. The powdered ingredients of cement were mixed and divided into two portions, the first portion being treated with energized water made from the unimproved device, and the second portion being treated with energized water made from the improved device. The amounts of water used to treat the two cement portions were equal and as specified in the instructions included on the container of cement powder. After sufficient water was added, the drying time of each portion of the cement was measured. The drying time for the cement was 3–4 hours when using the water treated with the improved device and approximately 12 hours when using water treated with the unimproved device. The improved device comprised an electrostatic signal generator such as that disclosed in the Binger '446 Patent and two Rf signal generators, a first Rf signal generator creating a 1.25 kilohertz signal and a second Rf signal generator creating a 1.5 kilohertz signal. In addition, the improved device comprised a single antenna and no signal boosters. The device of the Binger '446 Patent without the improvement was used as the unimproved device.

EXAMPLE 2

Octane Rating in Gasoline

The impact of treating gasoline with an unimproved device versus an improved device was evaluated as follows. An electrostatic device was placed between a reservoir tank and a receiving tank and gasoline was passed from the reservoir tank through an electrostatic device and into the receiving tank. After treatment, the octane rating of the gasoline was measured as previously described. The initial octane rating for the untreated gasoline was 87% and for the gasoline treated by the unimproved device was 87%; however, the octane rating for the gasoline treated by the improved device was 92.2%, indicating a dramatic increase in the octane rating. Accordingly, the improved device of the invention can be used to increase the octane rating of gasoline by at least 5% thereby increasing the octane rating from that of regular gasoline to premium gasoline. In the present example, the unimproved device was the electrostatic signal generator disclosed in the Binger '446 Patent, and the improved device comprised the same electrostatic signal generator and further comprised two Rf signal generators, the first of which generated a 1.1 kilohertz signal and the second of which generated a 1.5 kilohertz signal. The improved device further comprised a stainless steel antenna, and no signal boosters were required to achieve these results. It will be understood that the flow rate of gasoline through the improved device may have, but was not observed to have, an effect upon the efficiency of energizing the gasoline.

EXAMPLE 3

Combustion of a Fluid With a Stack

The use of an unimproved versus an improved electrostatic device in the combustion of a fluid influent stream in a stack was evaluated as follows. A stack was preheated and run under normal operating conditions. An influent stream of fluid to be combusted was injected into the stack and combusted therein, and the stack temperature, carbon dioxide emission level, smoke emission, combustion efficiency, and flame appearance were determined. The influent liquid was injected into the stack at a rate of one gallon per hour for each test run. The table below summarizes the results obtained wherein Test 1 and Test 2 were conducted with the unimproved equipment and Test 3 was conducted with the improved equipment.

| PARAMETER (Spec. value) | TEST ONE | TEST TWO | TEST THREE |
|---|---|---|---|
| NOZZLE SIZE IGPH @ 60 DEGREES F. | 1GPH | 1GPH | 1GPH |
| STACK TEMP: 550 DEGREES F. | 590° F. | 600° F. | 550° F. |
| $CO_2$: 10% | 10% | 10% | 8% |
| SMOKE: 1% (10,000 ppm) | 1% | TRACE | NONE OBSERVED |
| EFF: 75.5% | 75.50% | 75.50% | 71% |
| FLAME: ORANGE/GOLD | YELLOW/ GOLD | YELLOW/ GOLD | BRIGHT YELLOW/ GOLD |
| PATTERN: ERRATIC | GOOD | GOOD | EXCELLENT |

Accordingly, the improved device of the invention could be used in the combustion of a fluid in a stack to reduce required stack temperature, reduce carbon dioxide emission level, reduce smoke formation, and increase flame efficiency.

EXAMPLE 4

Milk Production

The use of the unimproved device versus the improved device in the production of milk in dairy cattle was evaluated as follows. Dairy cattle were divided into two groups and each group was given free access to a tank containing water. The first tank contained water treated by the unimproved device as disclosed in the Binger '446 Patent and the second contained water treated with the improved device as disclosed herein. The improved device comprised the electrostatic generator of the Binger '446 Patent and three Rf signal generators, a dual antenna array, and three signal boosters. The first, second and third Rf signal generators created Rf signals of 1.25, 1.38, and 2.1 kilohertz respectively. The results indicated that cattle consuming energized water prepared with the unimproved device produced on the average of 60.5 pounds of milk per day; whereas, cattle consuming energized water prepared with the improved device of the invention produced on the average of 67.05 pounds of milk per day. Accordingly, the improved device of the invention could be used to increase the production of milk in dairy cattle by at least five and preferably at least 10% per day. It was also observed that when cattle were given free access to both the first and second tanks, the cattle preferentially drank water from the second tank containing energized water prepared with the improved device of the invention. Further, the cattle drinking energized water from the improved device drank more water and generally displayed better health than those cattle drinking water prepared by the unimproved device.

EXAMPLE 5

Juice Production

The use of an unimproved electrostatic device versus an improved electrostatic device according to the invention in the production of juice was evaluated as follows. Juice syrup or concentrate was divided into two portions, the first portion being treated with the unimproved device of the Binger '446 Patent and the second portion being treated with the improved device. In a similar fashion, water was divided into two portions to create a first portion treated with the unimproved device, and the second portion being treated with the improved device. The respective first portions and second portions were combined to form a first juice treated with the unimproved device and a second juice treated with the improved device. Using a taste test as the discerning criterion in evaluating the difference between the first and second juices, it was determined that at least 2% and preferably at least 4% by volume less juice syrup was required in the second juice in order to make the second juice taste substantially the same as the first juice. Accordingly, the improved device of the invention can be used to reduce the amount of juice syrup, or concentrate, required to make a juice product from the juice concentrate. This reduction in the demand of juice, syrup or concentrate results in a financial savings for the manufacture of the juice since less juice syrup, or concentrate, will be required to produce a final commercially acceptable juice. A first improved device of the invention comprises an electrostatic signal generator, a first Rf signal generator which creates a 1.1 kilohertz signal, a second Rf signal generator which creates a 1.5 kilohertz signal, and a stainless steel antenna, the improved device does not require a signal booster although it can include one or more signal boosters.

EXAMPLE 6

The Killing of Coliform Bacteria

The use of an improved device versus an unimproved device in the killing of bacteria was evaluated as follows. An electrostatic generator such as disclosed in the Binger '446 Patent was used as the unimproved device, and the same electrostatic signal generator was improved by adding to it a first Rf signal generator which creates a 1.15 kilohertz signal, a second Rf signal generator which creates a 1.3 kilohertz signal, an antenna, and two signal boosters. A bacterial suspension in water containing approximately 26,600 coliform cells per 100 mL of solution was divided into two portions. The first portion was treated with the unimproved device, and the second portion was treated with the improved device. When the first portion was treated with the unimproved device, little to no cell death was observed; however, when the second portion was treated with the improved device, the bacterial cell count dropped down to less than approximately one coliform cell per 100 mL of solution which is equivalent with potable water. Accordingly, the improved device of the present invention can be used to significantly reduce the amount of bacterial load in a solution containing a high load of bacteria, and more specifically it can be used to generate potable water from a solution containing 20,000 or 25,000 coliform cells per 100 mL of solution. It will be understood that the improved device of the invention can be used to lyse or kill any type of microbes found in fluids containing fecal waste or raw sewage.

EXAMPLE 7

Barley Silage Production

The use of an unimproved versus improved device in the production of barley silage was determined as follows. The unimproved device was the same as that used in the previous examples; however, the improved device comprised a voltage spike signal generator, four Rf signal generators, a stainless steel antenna, and two signal boosters. The first, second, third and fourth Rf signal generators created Rf signals corresponding to 1.1 kilohertz, 1.5 kilohertz, 1.8 kilohertz, and 2.1 kilohertz, respectively. A field of barley was divided into two sections, the first section of which received water treated with the unimproved device and the second section of which received energized water prepared with the improved device of the invention. Each section was watered as needed to promote plant growth and maintain plant health. During harvest, the barley produced from the first and second sections of the field was measured, and it was determined that the barley crop obtained from the second section of the field was 72% larger by weight than the barley crop obtained from the first section of the field. Accordingly, the improved device of the invention can be used to increase grain production by at least 25%, preferably at least 50%, and more preferably at least 70% above grain production which is achieved using water not treated with the improved device. It was also noted that the barley crop in the second section had significantly less insect damage than the barley crop in the first section.

EXAMPLE 8

Feed Grass Production

Part A

The use of an unimproved versus improved device in the production of feed grasses was evaluated as follows. An unimproved device such as used in the previous example was used herein and further improved according to the invention by the addition of four Rf signal generators, a stainless steel antenna, and six signal boosters. The first, second, third, and fourth Rf signal generators created Rf signals including 1.1 kilohertz, 1.5 kilohertz, 1.8 kilohertz, and 2.1 kilohertz, respectively. The quality of the feed grass, which in the present example included Rhodes grass, was evaluated by measuring the nitrogen and protein content of the grass after harvesting. The results indicated that the Rhodes grass harvested from the field receiving water treated with the unimproved device had a nitrogen content of 1.8% and a protein content of 11.25%. However, the grass harvested from the field receiving the energized water prepared with the improved device contained a nitrogen content of 2.6% and a protein content of 16.25%. Each field received only the amount of water required to keep the grass healthy and growing. It is well known that feed grasses having higher nitrogen and protein concentrations are preferred over those with lower nitrogen and protein concentrations. Accordingly, the improved device of the invention can be used to increase the nitrogen content and protein content in feed grasses.

Part B

A field containing alfalfa was divided into two sections wherein the first section received water prepared with the unimproved device above and the second section received energized water prepared with the improved device of the invention. The effect of the water upon the quality of the alfalfa was evaluated by determining the moisture content, protein content, and crude fiber content of the alfalfa after it was harvested. The first and second sections of the field were irrigated with the respective waters as needed to promote plant growth and maintain plant health. The harvested alfalfa obtained from the first section had a moisture content of 56.08%, a crude protein content of 19.5%, and a crude fiber content of 31.5%. The alfalfa contained from the second section had a moisture content of 80.63%, a crude protein content of 25.3%, and a crude fiber content of 22.6%. Accordingly, the improved device of the invention can be used to increase the moisture content and protein content of the feed grass and simultaneously reduce the fiber content of the feed grass as compared to the feed grass irrigated with water not prepared with the improved device of the invention. A feed grass having a high moisture and protein content and a reduced fiber content is preferred by cattle feeders since it facilitates digestion and provides greater nutrition to cattle. The improved device in the present example incorporated a double antenna array rather than a single antenna as described in Part A above.

EXAMPLE 9

Shrimp Production

The use of an improved device according to the invention was evaluated in the production of nursery grown shrimp. Ten 5-acre ponds were stocked with brine shrimp (about 1.5 lbs.; ~700,000 shrimp). The ponds were divided into groups A and B which received regular unenergized salt water and energized salt water, respectively. The survival rate, time-to-market, weight of shrimp produced per acre of pond, and the food conversion rates were monitored and or determined. The survival rate is a measure of how many of the initial brine shrimp survived until harvest of the shrimp. A higher survival rate is preferred. The time-to-market is measure of how many weeks it takes for the shrimp to reach an acceptable weight at which time they are harvested and brought to market. A lower time-to-market is preferred. The food conversion rate is a measure of how much food the shrimp require in order to maintain optimal growth and maximize production. The shrimp were fed grains such as cattle feed. A lower food conversion rate is desired. The results are summarized below.

| Group | Survival Rate (%) | Time-to-Market (wks.) | Production (lbs./acre) | Food Convesion Rate |
|---|---|---|---|---|
| A | 60 | 20.2 | 4015 | 2.56 |
| B | 92 | 18.3 | 5985 | 2.19 |

The improved device of the invention used to achieve these results include first, second, third and fourth Rf signal generators that generated the following Rf signals: 1100, 1500, 1800 and 2100 KHz, respectively. The device also included an electrostatic signal signal generator and a three antenna array. A signal booster was not required but can be used if desired.

It will be understood, in view of the above data, that the device of the invention and energize water made therewith can be used to increase the production of, increase the survival rate of, reduce the feed requirement of and reduce the time-to-market of nursery grown salt water shrimp.

Although preferred embodiments of the present invention have been described in the foregoing Detailed Description and illustrated in the accompanying drawings, it will be understood that the invention is not limited to the embodiments disclosed, but is capable of numerous rearrangements, modifications, and substitutions of parts and elements without departing from the spirit of the invention. Accordingly, the present invention is intended to encompass such rearrangements, modifications, and substitutions of parts and elements as fall within the scope of the appended claims.

I claim:

1. An electrostatic device for converting source fluids to energized fluids, said device comprising:

a fluid conduit;

a voltage spike signal generator for generating at least one voltage spike signal;

at least first and second radio frequency Rf signal generators for generating at least two different Rf signals having controlled frequencies; and at least one antenna disposed in said fluid conduit for emitting at least two different Rf signals having controlled frequencies:

wherein:

said at least one antenna emits into a source fluid in said fluid conduit a combination signal comprising said at least one voltage spike signal and said at least two different Rf signals to form an energized fluid which can provide a measurable benefit to at least one of a living organism, machinery, equipment, process, and substance.

2. The device of claim 1 further comprising at least one signal booster which boosts the amplitude of at least one of said combination signal and said at least two different Rf signals having controlled frequencies.

3. The device of claim 1, wherein each of said at least first and second Rf signal generators can form a respective combination sub-signal comprising at least one controlled Rf signal and at least a portion of said voltage spike signal.

4. The device of claim 3, wherein at least one of said first and second Rf signal generators can also perform at least one of the following functions:

split the voltage spike signal into two or more different voltage spike subsignals;

invert the voltage spike signal;

amplify the voltage spike signal; and multiply the voltage spike signal.

5. The device of claim 3 further comprising one or more signal boosters adapted to boost the amplitude or voltage of one or more of said combination signal, said at least one voltage spike signal, said combination sub-signal and one or more of said at least two different Rf signals.

6. The device of claim 1 wherein a frequency of said voltage spike signal has a frequency which is at least tenfold less than the frequency of an Rf signal.

7. The device of claim 1 wherein said at least one antenna is an antenna array comprising two or more antennas disposed in said fluid conduit.

8. The device of claim 1, wherein said fluid conduit comprises an influent port and an effluent port.

9. The device of claim 1 wherein said voltage spike signal and said two or more different Rf signals are synchronized.

* * * * *